(12) United States Patent
Bulla, Jr. et al.

(10) Patent No.: US 6,928,368 B1
(45) Date of Patent: Aug. 9, 2005

(54) GENE MINING SYSTEM AND METHOD

(75) Inventors: Lee A. Bulla, Jr., Tioga, TX (US);
Mehmet Candas, Dallas, TX (US)

(73) Assignee: The Board Regents, The University of Texas System, Austin, TX (US)

( * ) Notice: Subject to any disclaimer, the term of this patent is extended or adjusted under 35 U.S.C. 154(b) by 376 days.

(21) Appl. No.: 09/696,801

(22) Filed: Oct. 25, 2000

Related U.S. Application Data

(60) Provisional application No. 60/161,571, filed on Oct. 26, 1999, and provisional application No. 60/161,527, filed on Oct. 26, 1999.

(51) Int. Cl.[7] .................. G01N 33/48; G06F 19/00; C07H 21/00

(52) U.S. Cl. .................. 702/19; 702/20; 536/24.33

(58) Field of Search .................. 702/19, 20; 536/24.33

(56) References Cited

U.S. PATENT DOCUMENTS

| | | | |
|---|---|---|---|
| 5,962,643 A | | 10/1999 | Sheppard et al. |
| 5,966,712 A | | 10/1999 | Sabatini et al. ............. 707/104 |
| 6,274,319 B1 | * | 8/2001 | Messier et al. ................ 435/6 |
| 6,303,297 B1 | * | 10/2001 | Lincoln et al. ................ 435/6 |

OTHER PUBLICATIONS

Rose et al. (Nucleic Acids Research (1998) vol. 26, No. 7, pp. 1628–1635).*

Davids, B.J. et al. (1999) *Gene* (Elsevier Biomedical Press, Amsterdam) 228(1–2):213–223.

Mackrell, A.G. et al. (1988) *PNAS USA* 85(8):2633–2637.

* cited by examiner

*Primary Examiner*—Marjorie Moran
*Assistant Examiner*—Lori A. Clow
(74) *Attorney, Agent, or Firm*—Morrison & Foerster LLP

(57) ABSTRACT

The present invention provides a system, method and apparatus for targeting gene sequences having one or more phenotypic characteristics using a computer. One or more phenotypic characteristics are selected. A gene sequence is then selected that is known to have the selected phenotypic characteristics. In addition, one or more databases containing cataloged gene sequences are selected. The selected gene sequence is compared to the cataloged gene sequences, and any cataloged gene sequences that contain a portion of the selected gene sequence are extracted. The selected gene sequence is aligned to each portion of the extracted gene sequence and the extracted gene sequences are prioritized based on the alignment of the selected gene sequence. At least one of the prioritized gene sequences is selected based on one or more phenotypic criteria. Finally, one or more degenerate primers are designed to target the selected-prioritized gene sequences.

20 Claims, 12 Drawing Sheets

GENE MINING SYSTEM AND METHOD

CROSS-REFERENCES TO RELATED APPLICATIONS

This Application for Patent claims the benefit of priority from, and hereby incorporates by reference the entire disclosure of, co-pending U.S. Provisional Application for patent Ser. No. 60/161,527, filed Oct. 26, 1999; and Ser. No. 60/161,571, filed Oct. 26, 1999.

TECHNICAL FIELD OF THE INVENTION

This invention relates to the targeted isolation of biologically and functionally relevant gene and genomic information and bioinformatics and more particularly to a system, method and apparatus for targeting and cloning gene sequences based on functional observations from data mined from available gene databases.

BACKGROUND OF THE INVENTION

Without limiting the scope of the invention, its background is described in connection with uses of functional genomics and bioinformatics, as an example.

The present invention relates generally to methods and systems for searching and identifying functional nucleic acid sequences and proteins encoded by genes available from the multitude of nucleic acid and protein databases presently available. These biological databases store information that is searchable and from which biological information may be retrieved. More particularly, the present invention relates to systems and methods for identifying biologically relevant sequences of biological molecules using an integrated approach that specifically identifies sequences for cloning.

Generally, informatics may be defined as the study and application of computer and statistical techniques to the management of information. In projects related to biological information, the term "bioinformatics" has been coined to include the development of methods to, e.g., search databases, analyze nucleic acid sequence information, predict protein sequence, protein structure, and protein function from nucleic acid sequence data.

The widespread use and availability of molecular biological techniques have allowed for the rapid development and identification of nucleic acid derived sequences. With the widespread availability of advanced computer systems and the integration of laboratory equipment with computer software, researchers are able to conduct advanced quantitative analyses, database comparisons and computational algorithms to seek and identify gene sequences with homology to known sequences.

Examples of large-scale sequencing and the availability of genetic information for a number of organisms have been cataloged in a number of public and private computer databases. Genetic databases for organisms such as *Escherichia coli, Haemophilus influenzae, Mycoplasma genitalium*, and *Mycoplasma pneumoniae*, to name a few, are publicly available. At present, however, complete sequence data is available for relatively few species, and the ability to manipulate sequence data within and between species and databases is greatly limited by the ability of these public databases to be searched for functional significance.

One example of a system for comparing relational databases of sequences is disclosed in U.S. Pat. No. 5,966,712, issued to Sabatini, et al. The system disclosed is a relational database system for storing and manipulating biomolecular sequence information and includes a database of genomic libraries for a plurality of types of organisms. These libraries are taught to have multiple genomic sequences, at least some of which represent open reading frames located along a contiguous sequence in each of the plurality of organisms' genomes. A user interface is provided and is capable of receiving a selection of two or more of the genomic libraries for comparison and displaying the results of the comparison. The system also provides a user interface capable of receiving a selection of one or more probe open reading frames for use in determining homologous matches between such probe open reading frame(s) and the open reading frames in the genomic libraries, and displaying the results of the determination.

Also needed are fully integrated systems that take advantage of functional observations and the identification of biologically relevant and functional gene sequences. This disconnect between genotype and phenotype leads to the pursuit of many genes of doubtful relevance or even mere artifacts. Thus, researchers are presently unable to avoid using available computer resources to explore, identify and study relevant gene sequences, gene expression, and molecular structure without extensive experimentation.

Another such use of bioinformatics involves studying an organism's genome to determine the sequence and placement of its genes and their relationship to other sequences and genes within the genome or to genes in other organisms. The study of the relationship between introns and exons, for example across species, allows for a scientific understanding of many underlying substructures of the protein or proteins being expressed. It also allows for the identification of sequences that are involved in the regulation of the gene or genes that are at a particular gene locus. Such information may be of significant interest in biomedical and pharmaceutical research to assist in the evaluation of potential drug efficacy and resistance for genes that are well studied and for which significant structure-function studies have been conducted. In one such database system (Incyte Pharmaceuticals, Inc., U.S.A.), software has been developed that searched the annotated information that is part of genomic sequence data in publicly available sequence databases. Unfortunately, not all electronically recorded sequences contain annotated information. Some contain information that is not functional, contain information that is not accurate, or contain information that has no relation to function. Examples of such databases include the widely available public databases GenBank (NCBI) and TIGR. Therefore, the accuracy and relevance of any search results from these databases often has no bearing on the cellular biological function of a particular protein of gene regulatory element.

Although genetic data processing and relational database systems such as those developed by Incyte Pharmaceuticals, Inc. provide great power and flexibility in analyzing genetic information, this area of technology is still in its infancy and further improvements in genetic data processing and relational database systems will help accelerate biological research for numerous applications.

SUMMARY OF THE INVENTION

While publicly available databases make manipulation of gene and genomic information easy to perform and understand, sophisticated computer database systems have not been developed that begin their searching based on functional biologically-relevant information. Furthermore, a need has been recognized for the identification, isolation and cloning of biologically relevant genes and genomic information mined from available resources. While large amounts of sequence data are being generated as part of the Human Genome Project and other like projects, a coordinated system and method for culling functionally relevant sequences is needed. Also needed are systems and methods for mining genes based on the observation of biologic data, for which an understanding of the genetic basis for the observation is known or unknown.

The present invention provides a method for targeting gene sequences having one or more genotypic or phenotypic characteristics using a computer. One or more genotypic or phenotypic characteristics are selected. A gene sequence is then selected that is known to have the selected phenotypic characteristics. In addition one or more databases containing cataloged gene sequences are selected. The selected gene sequence is compared to the cataloged gene sequences, and any cataloged gene sequences that contain a portion of the selected gene sequence are extracted. The selected gene sequence is aligned to each portion of the extracted gene sequence and the extracted gene sequences are prioritized based on the alignment of the selected gene sequence. At least one of the prioritized gene sequences is selected based on one or more phenotypic criteria. Finally, one or more degenerate primers are designed to target the selected-prioritized gene sequences.

The present invention also provides a computer program embodied on a computer-readable medium that performs the steps described above. In addition, the present invention provides a system having a computer, one or more databases containing the cataloged gene sequences, and a communication link connecting the computer to the one or more databases. The computer is used to select one or more phenotypic characteristics, select a gene sequence that is known to have the selected phenotypic characteristics, compare the selected gene sequence to the cataloged gene sequences, extract any cataloged gene sequences that contain a portion of the selected gene sequence, align the selected gene sequence to each portion of the extracted gene sequence, prioritize the extracted gene sequences based on the alignment of the selected gene sequence, select at least one of the prioritized gene sequences based on one or more phenotypic criteria, and design one or more degenerate primers to target the selected-prioritized gene sequences.

Thus, the present invention takes the current state of the art, which requires combing GenBank with individual sequences to discover all of the homologous sequence, to a fully automated system that includes not only sequence parameters in the search, but includes other search parameters like species, protein characteristics and functional domains. Further, multiple homology search algorithms are seamlessly incorporated into the method. This not only allows nucleotide or amino acid searches to be performed, but allows any conceivable type of search algorithm to be employed without requiring the user to do more than select the desired parameters. In this way, multiple types of databases (e.g., nucleotide, amino acid, 3D structure, etc.) can be searched, even simultaneously if desired.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE PRESENTLY PREFERRED EXEMPLARY EMBODIMENTS

Figure 1:
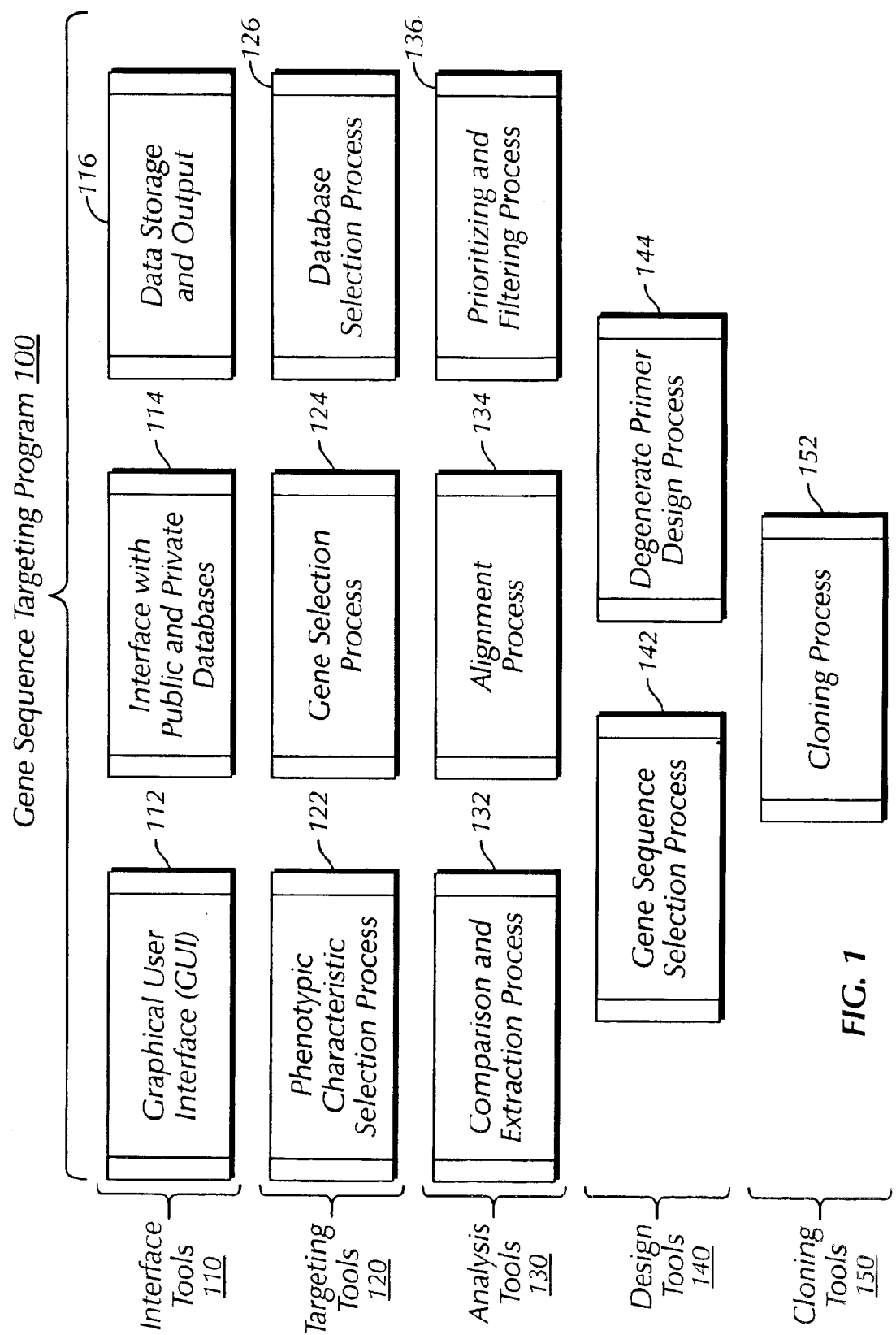
FIG. 1 is a block diagram showing some features of the present invention.

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

While the making and using of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and do not delimit the scope of the invention.

DEFINITIONS

As used throughout the present specification the following abbreviations are used: TF, transcription factor; ORF, open reading frame; kb, kilobase (pairs); UTR, untranslated region; kD, kilodalton; PCR, polymerase chain reaction; RT, reverse transcriptase.

The term "x % homology" refers to the extent to which two nucleic acid or protein sequences are complementary as determined by BLAST homology alignment as described by T. A. Tatusova & T. L. Madden (1999), "Blast 2 sequences—a new tool for comparing protein and nucleotide sequences", FEMS MICROBIOL LETT. 174:247–250 and using the following parameters: Program (blastn) or (blastp) as appropriate; matrix (OBLOSUM62), reward for match (1); penalty for mismatch (–2); open gap (5) and extension gap (2) penalties; gap x-drop off (50); Expect (10); word size (11); filter (off). An example of a web based two sequence alignment program using these parameters is found at the world wide web address:ncbi.nlm.nih.gov/gorf/b12.html.

The invention thus includes nucleic acid or protein sequences that are highly similar to the sequences of the present invention, and include sequences of 80, 85, 90, 95 and 98% similarity to the sequences described herein.

The invention also includes nucleic acid sequences that can be isolated from genomic or cDNA libraries or prepared synthetically, that hybridize under high stringency to the entire length of a 400 nucleotide probe derived from the nucleic acid sequences described herein under. High stringency is defined as including a final wash of 0.2×SSC at a temperature of 60° C. Under the calculation:

$$\mathit{Eff}\ T\ m = 81.5 + 16.6(\log M\ [Na+]) + 0.41(\%\ G+C) - 0.72(\%\ \text{formamide})$$

the percentage allowable mismatch of a gene with 50% GC under these conditions is estimated to be about 12%.

Primers are commercially available from the Clontech SMART™ cDNA Library Construction Kit (SMART III Oligonucleotide; 5' PCR Primer; CDS III/3' PCR Primer; CDS III/3' TRUN).

Tools

Alignment tools for use with the present invention may include, e.g., BLAST. BLAST (Basic Local Alignment Search Tool) is a heuristic search algorithm employed by the programs blastp, blastn, blastx, tblastn, and tblastx. This combination of programs use the statistical methods of Karlin and Altschul (1990, 1993). More recent versions of the program allow for tailoring of the sequence similarity during a searching, e.g., to identify homologs in a query sequence. The programs are not generally useful for motif-style searching.

The fundamental unit of BLAST algorithm output is the High-scoring Segment Pair (HSP). An HSP includes two sequence fragments of arbitrary but equal length whose alignment is locally maximal and for which the alignment score meets or exceeds a threshold or cutoff score. A set of HSPs is thus defined by two sequences, a scoring system, and a cutoff score. This HSP set may be empty if the cutoff score is sufficiently high. In the software implementation of the BLAST algorithm, each HSP has a segment from the query sequence and one from a database sequence. The sensitivity and speed of the programs may be adjusted using the standard BLAST algorithm parameters W, T, and X (Altschul et al., 1990). Furthermore, the selectivity of the programs may be adjusted via the cutoff score.

The approach to similarity searching taken by the BLAST programs is first to look for similar segments (HSPs) between the query sequence and a database sequence. Next, the statistical significance of any matches that were found is evaluated. Finally, those matches that satisfy a user-selectable threshold of significance are reported. The finding of multiple HSPs involving the query sequence and a single database sequence are treated statistically in a variety of ways. Another problem with standard BLAST is that it uses the default programs devised for "Sum" statistics (Karlin and Altschul, 1993), as such, the statistical significance ascribed to a set of HSPs may be higher than that of any individual member of the set. Only when the ascribed significance satisfies the user-selectable threshold will the match be reported to the user.

The task of finding HSPs begins by identifying short words of length W in a query sequence that either match or satisfy some positive-valued threshold score T when aligned with a word of the same length in a database sequence. The identification of the first short word as a location to initiate a search is one of the limitations of the BLAST search, as it identifies a first location to initiate an alignment and anchors its alignment at that location. By prefiltering sequences such that irrelevant sequences are removed, a priori, even the BLAST alignment tool may be used with the present invention. Furthermore, by pre-filtering the search sequences, open database BLAST searching is made more efficient by limiting search parameters to those that are functional rather than artifactual. Removal of artifactual sequences from the potential search pool further aids in the location of relevant genes due, to the limit of search results imposed by BLAST to 50 potential sequences. T is referred to as the neighborhood word score threshold (Altschul, et al., 1990). These initial neighborhood word hits act as seeds for initiating searches to find longer HSPs containing them. The word hits are extended in both directions along each sequence for as far as the cumulative alignment score may be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached.

A Maximal-scoring Segment Pair (MSP) is defined by two sequences and a scoring system and is the highest-scoring of all possible segment pairs that can be produced from the two sequences. The statistical methods described by Karlin and Altschul (1990, 1993) may be used to determine the significance of MSP scores in the limit of long sequences, under a random sequence model that assumes independent and identically distributed choices for the residues at each position in the sequences. These statistics may be modified by the filtering of the present invention to the task of assessing the significance of HSP scores obtained from comparisons of pre-filtered potentially short, biological sequences.

The five BLAST programs described here perform the following tasks: blastp compares an amino acid query sequence against a protein sequence database; blastn compares a nucleotide query sequence against a nucleotide sequence database; blastx compares the six-frame conceptual translation products of a nucleotide query sequence (both strands) against a protein sequence database; and tblastn compares a protein query sequence against a nucleotide sequence database dynamically translated in all six reading frames, also for both strands. More particularly, tblastx compares the six-frame translations of a nucleotide search query sequence against the six-frame translations of a nucleotide sequence database.

BLAST restricts the number of short descriptions of matching sequences reported to the number specified; default limit is 100 descriptions. During the alignment procedure, BLAST restricts database sequences to the number of specified high-scoring segment pairs (HSPS) that are requested and thereby limits its reporting function. The default HSP limit is 50. If more than 50 database sequences satisfy the statistical significance threshold for reporting, BLAST only matches and reports those sequences given the greatest statistical significance.

The statistical significance threshold (EXCEPT value) for reporting matches against database sequences is 10, such that 10 matches are expected to be found merely by chance, according to the stochastic model of Karlin and Altschul (1990). If the statistical significance ascribed to a match is greater than the EXPECT threshold, the match will not be reported. Dower EXPECT thresholds are more stringent, leading to fewer chance matches being reported. Fractional values are acceptable.

The Cutoff score for reporting high-scoring segment pairs is calculated from the EXPECT value. HSPs are reported for a database sequence only if the statistical significance ascribed to them is equal to or greater that the HSP ascribed to a lone HSP having a score equal to the CUTOFF value.

Higher CUTOFF values are more stringent, leading to fewer chance matches being reported. Typically, significance thresholds may be more intuitively managed using EXPECT.

Another function of BLAST is MATRIX. MATRIX is an alternative scoring matrix for BLASTP, BLASTX, TBLASTN and TBLASTX. The default matrix is BLOSUM62 (Henikoff & Henikoff, 1992). The valid alternative choices include:

PAM40, PAM120, PAM250 and IDENTITY. No alternate scoring matrices are available for BLASTN; specifying the MATRIX directive in BLASTN requests returns an error response. The STRAND function of BLAST restricts a TBLASTN search to just the top or bottom strand of the database sequences; or restrict a BLASTN, BLASTX or TBLASTX search to just reading frames on the top or bottom strand of the query sequence. The FILTER function of BLAST is limited to "mask off" segments of the query sequence that have low compositional complexity, as determined by the SEG program of Wootton & Federhen (Computers and Chemistry, 1993), or segments having short-periodicity internal repeats, as determined by the XNU program of Claverie is & States (Computers and Chemistry, 1993), or, for BLASTN, by the DUST program. Filtering may eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "NO" in nucleotide sequence (e.g., "NNNNNNNNNNNNN") and the letter "X" in protein sequences (e.g., "XXXXXXXXX"). Users may turn off filtering by using the "Filter" option on the "Advanced options for the BLAST server" page.

Furthermore, filtering is only applied to the query sequence (or, its translation products), not to database sequences. Default filtering is DUST for BLASTN, SEG for other programs. It is not unusual, however, for nothing at id all to be masked using the filter function of BLAST because filtering does not always yield an effect. Furthermore, in some cases, sequences are masked in their entirety, indicating that the statistical significance of any matches reported against the unfiltered query sequence should be suspect.

An alternative database searching engine for use with the present invention is another legacy system known as Clustal W. The Clustal W algorithm is basically the same as for Clustal V. Clustal W improves on the original Clustal V program, by eliminating terminal gap penalization, thereby treating them the same as all other gaps. By freeing the calculation of terminal gaps the alignment is improved by eliminating single residues jumping to the edge of the alignment.

The change in alignment scheme, however, is not without caveats, namely that a gap near the end of the alignment causes Clustal W to insert a gap thereby reducing the alignment score. By freeing terminal gaps, therefore, the overall score of an otherwise good alignment is reduced. In operation, the misalignment may be reduced by lowering the gap opening and reducing the extension penalties. It is difficult, however, to weight the balance between these two functions. The pre-filtering function of the present invention allows the user to eliminate the need to determine which of the alignment penalties to conform to by reducing the need to penalize otherwise good alignments. The present invention allows for maximum specificity and selectivity to be applied to pre-screened or filtered sequences.

One great advantage of the Clustal W program is the speed of the initial pairwise alignments. The speed of the alignment in all programs, including BLAST and others, is always commensurate with a decrease in specificity. Therefore, alignment quality is compromised for speed. Clustal W allows for a slower search speed that increases the accuracy of the alignment. By default, the initial pairwise alignments of Clustal W are carried out using a full dynamic programming algorithm. This initial pairwise alignment is more accurate than the older hash/k-tuple based alignments (Wilbur and Lipman) but is somewhat slower. On a fast workstation the difference in speed is often not noted. When searching larger and larger databases or clusters of databases, however, the improved filtering and searching system of the present invention greatly increases both accuracy and speed.

Another option of Clustal W is the ability to delay the alignment of distant sequences. The user may set a cut-off to delay the alignment of the most divergent sequences in a data set until all other sequences have been aligned. This delay in distant alignment is particularly useful when screening genomic sequences and is important when assessing the intron/exon junctions and intron repeats across species lines. In Clustal W the default is set to 40%, which means that if a sequence is less than 40% identical to any other sequence, its alignment will be delayed Clustal W also allows for the iterative realignment and for resetting gaps between alignments. By default, the alignment of a set sequences a second time (e.g., with changed gap penalties), causes the gaps from the first alignment to be discarded. Discarding the older gaps from previous alignment often provides a better alignments by keeping the gaps (do not reset them) and doing the full multiple alignment a second time. Sometimes, the alignment will converge on a better solution, alternatively, it is possible for the new alignment will be the same as the first.

Clustal W also allows for sequence profile alignments. By profile alignment, it is meant the alignment of old alignments/sequences. In this context, a profile is just an existing alignment (or even a set of unaligned sequences). The use of a profile alignment allows the user to read in an old alignment (in any of the allowed input formats) and align one or more new sequences to that profile. The profile Ad alignment may be a full alignment or a single sequence alignment. In the simplest mode, the user simply aligns the two profiles to each other. This cross-profile alignment is useful 1% to gradually build up a full multiple alignment.

A second option is to align the sequences from, e.g., a second profile, one at a time to the first profile. This is done by taking into account the underlying sequence comparison tree between the sequences. The second profile alignment is useful if the user has a set of new sequences (not aligned) and wish to add them all to an older alignment.

Examples of databases that may be used to prescreen for sequences include both public and private databases of either nucleic acid or protein sequences. As will be understood by those of skill in the art, nucleic acids generally may be either ribonucleic acids or deoxyribonucleic acids, or derivatives or variants thereof.

One such database is ACEDB. Acedb is a genome database system developed over the last 7 years primarily by Jean Thierry-Mieg (CNRS, Montpellier) and Richard Durbin (Sanger Centre). It provides a custom database kernel, with a non-standard data model designed specifically for handling scientific data flexibly and a graphical user interface with n=many specific displays and tools for genomic data.

Acedb may be used for both managing data within genome projects, and for making genomic data available to other scientists. Acedb was originally developed for the C.elegans genome project, from which its name was derived (A C.elegans DataBase). The tools in it have been generalized to allow for greater flexibility to the point that the same software is now used for many different genomic databases from, e.g., bacteria, fungi, plants to man. It is also increasingly used for databases with non-biological content, e.g., vectors and viruses.

The acedb software is primarily developed to run under the Unix operating system, using X-Windows for graphics. Copies of the software are accessible via FTP sites, or may be interfaced EU through a Web interface, which serves a number of human databases as well as the AceBrowser system, which serves a local installation of the C.elegans Genome Database.

Referring to FIG. 1, a block diagram shows some features of the present invention. The gene sequence targeting program 100 of the present invention comprises a variety of tool types, such as interface tools 110, targeting Ad tools 120, analysis tools 130, design tools 140, and cloning tools 150. These tools 110, 120, 130, 140 and 150 are preferably integrated together using an objected-oriented programming language.

The interface tools 110 may include a graphical user interface (GUI) 112, one or more interfaces with public and private databases 114, and data storage and output tools 116. The GUI 112 is preferably a menu driven interface that allows a user to jump between applications, point and click on selections, and view information in graphical form. The one or more interfaces with public and private databases 114 allow the program and the user to access, search and retrieve data from local and remote databases, which may be public or private. These interfaces 114 can be conFIGUREd to allow seamless access to a variety of disparate databases, such as publication databases and gene sequence databases. The data storage and output tools 116 may provide access to program help information, experimental documentation features, reports, project data storage, and data backup, import and export features.

The following sequence comparison software is available from the Genetics Computer Group (GCG) software and may be accessed by the system of the present invention.

Table I Sequence Retrieval-Interface Tools
  Fetch
  Copies GCG sequences or data files from the GCG database into your directory or displays them on your terminal screen.
  NetFetch
  Retrieves entries from NCBI listed in a NetBLAST output file. It can also be used to retrieve entries individually by entry name or accession number. The output of NetFetch is an RSF file.

The targeting tools 120 allow the user to set the parameters that will be used to target the gene sequence. These targeting tools 120 may include a phenotypic characteristics selection process 122, a gene process 124 and a database selection process 126. The phenotypic characteristics selection process 122, gene selection process 124 and database selection process 126 will be described below in more detail in reference to FIGS. 3, 4 and 5 respectively.

The following database searching software is available from the Genetics Computer Group (GCG) software and may be accessed by the system of the present invention.

Table II Database Searching-Targeting Tools
  Reference Searching
  LookUp
  Identifies sequence database entries by name, accession number, author, organism, keyword, title, reference, feature, definition, length, or date. The output is a list of sequences.
  StringSearch
  Identifies sequences by searching for character patterns such as "globin" or "human" in the sequence documentation.
  Names
  Identifies GCG® data files and sequence entries by name. It may show what set of sequences is implied by any sequence specification.

The analysis tools 130 generate results based on the information and preferences selected by user with the targeting tools 120 and then allow the user to analyze those results. The analysis tools 130 may include a comparison and extraction process 132, an alignment process 134 and a prioritizing and filtering process 136. These analysis tools 130 can be legacy systems.

The following analysis tools software is available from the Genetics Computer Group (GCG) software and may be accessed by the system of the present invention.

Table III Multiple Sequence Comparison-Analysis Tools
  Gap
  Uses the algorithm of Needleman and Wunsch to find the alignment of two complete sequences that maximizes the number of matches and minimizes the number of gaps.
  BestFit
  Makes an optimal alignment of the best segment of similarity between two sequences. Optimal alignments are found by inserting gaps to maximize the number of matches using the local homology algorithm of Smith and Waterman.
  FrameAlign
  Creates an optimal alignment of the best segment of similarity (local alignment) between a protein sequence and the codons in all possible reading frames on a single strand of a nucleotide sequence. Optimal alignments may include reading frame shifts.
  Compare
  Compares two protein or nucleic acid sequences and creates a file of the points of similarity between them for plotting with DotPlot. Compare finds the points using either a window/stringency or a word match criterion. The word comparison is 1,000 times faster than the window/stringency comparison, but somewhat less sensitive.
  DotPlot
  Makes a dot-plot with the output file from Compare or StemLoop.
  GapShow
  Displays an alignment by making a graph that shows the distribution of similarities and gaps. The two input sequences should be aligned with either Gap or BestFit before they are given to GapShow for display.
  ProfileGap
  Makes an optimal alignment between a profile and one or more sequences.
  Pileup
  Creates a multiple sequence alignment from a group of related sequences using progressive, pairwise alignments. It may also plot a tree showing the clustering relationships used to create the alignment.
  PlotSimilarity
  Plots the running average of the similarity among the sequences in a multiple sequence alignment.
  MEME (Multiple EM for Motif Elicitation) Finds motifs in a group of unaligned sequences. MEME saves these motifs as a set of profiles. A database-search of sequences with these profiles is then conducted using, e.g., the MotifSearch program.

ProfileMake

Creates a position-specific scoring table, called a profile, that quantitatively represents the information from a group of aligned sequences. The profile may then be used for database searching (ProfileSearch) or sequence alignment (ProfileGap).

ProfileGap

Makes an optimal alignment between a profile and one or more sequences.

Overlap

Compares two sets of DNA sequences to each other in both orientations using a WordSearch style comparison.

NoOverlap

Identifies the places where a group of nucleotide sequences do not share any common subsequences.

OldDistances

Makes a table of the pairwise similarities within a group of aligned sequences.

Table IV Database Searching-Analysis Tools

Sequence Searching

Blast

Searches for sequences similar to a query sequence. The query and the database searched may be either peptide or nucleic acid in any combination. BLAST can search databases on a local computer or databases maintained at the National Center for Biotechnology Information (NCBI) in Bethesda, Md., USA.

NetBLAST

Searches for sequences similar to a query sequence. The query and the database searched may be, either peptide or nucleic acid in any combination. NetBLAST can search only databases maintained at the National Center for Biotechnology Information (NCBI) in Bethesda, Md., USA.

FastA

Does a Pearson and Lipman search for similarity between a query sequence and a group of sequences of the same type (nucleic acid or protein). For nucleotide searches, FastA may be more sensitive than BLAST.

SSearch

Does a rigorous Smith-Waterman search for similarity between a query sequence and a group of sequences of the same type (nucleic acid or protein). This may be the most sensitive method available for similarity searches. Compared to BLAST and FastA, it is very slow.

TFastA

Does a Pearson and Lipman search for similarity between a protein query sequence and any group of nucleotide sequences. TfastA translates the nucleotide sequences in all six reading frames before performing the comparison. It is designed to answer the question, "What implied protein sequences in a nucleotide sequence database are similar to my protein sequence?"

TFastX

Does a Pearson and Lipman search for similarity between a protein query sequence and any group of nucleotide sequences, taking frameshifts into account. It is designed to be a replacement for TfastA, and like TfastA, it is designed to answer the question, "What implied protein sequences in a nucleotide sequence database are similar to my protein sequence?"

FastX

Does a Pearson and Lipman search for similarity between a protein query sequence and any group of nucleotide sequences. TfastA translates the nucleotide sequences in all six reading frames before performing the comparison. It is designed to answer the question, "What implied protein sequences in a nucleotide sequence database are similar to my protein sequence?"

FrameSearch

Searches a group of protein sequences for similarity to one or more nucleotide query sequences, or searches a group of nucleotide sequences for similarity to one or more protein query sequences. For each sequence comparison, the program finds an optimal alignment between the protein sequence and all possible codons on each strand of the nucleotide sequence. Optimal alignments may include reading frame shifts.

MotifSearch

Uses a set of profiles (representing similarities within a family of sequences) as a query to either a) search a database for new sequences similar to the original family, or b) annotate the members of the original family with details of the matches between the profiles and each of the members. Normally, the profiles are created with the program MEME.

ProfileSearch

Uses a profile (representing a group of aligned sequences) as a query to search the database for new sequences with similarity to the group. The profile is created with the program ProfileMake.

ProfileSegments

Makes optimal alignments showing the segments of similarity found by ProfileSearch.

FindPatterns

Identifies sequences that contain short patterns like GAATTC or YRYRYRYR. Patterns may be define ambiguously, thereby allowing for a greater number of mismatches. Patterns may be provided in a file or simply typed into a terminal.

Motifs

Looks for sequence motifs by searching through proteins for the patterns defined in the PROSITE® Dictionary of Protein Sites and Patterns. Motifs can display an abstract of the current literature on each of the motifs it finds.

WordSearch

Identifies sequences in the database that share large numbers of common words in the same register of comparison with your query sequence. The output of WordSearch can be displayed with Segments.

Segments

Aligns and displays the segments of similarity found by WordSearch.

LineUp

Is a screen editor for editing multiple sequence alignments. Up to 30 sequences may be edited simultaneously. New sequences may also be typed in by hand or added from existing sequence files. A consensus sequence identifies places where the sequences are in conflict.

Table V Fragment Assembly-Analysis Tools

GelStart

Begins a fragment assembly session by creating a new fragment assembly project or by identifying an existing project.

GelEnter

Adds fragment sequences to a fragment assembly project. It accepts sequence data from your terminal keyboard, a digitizer, or existing sequence files.

GelMerge

Aligns the sequences in a fragment assembly project into assemblies called contigs. The assembled contigs may be viewed and/or edited from the assemblies generated in GelAssemble.

GelAssemble

Is a multiple sequence editor for viewing and editing contigs assembled by GelMerge.

Gelview

Displays the structure of the contilas in a fragment assembly project.

GelDisassemble

Breaks up the contigs in a fragment assembly project into single fragments.

Table VI Gene Finding and Pattern Recognition-Analysis Tools

TeatCode

Helps you identify protein coding sequences by plotting a measure of the non-randomness of the composition at every third base. The statistic does not require a codon frequency table.

CodonPreference

Is a frame-specific gene finder that tries to recognize protein coding sequences by virtue of the similarity of their codon usage to a codon frequency table or by the bias of their composition (usually GC) in the third position of each codon.

Frames

Shows open reading frames for the six translation frames of a DNA sequence. Frames may superimpose the pattern of rare codon choices if you provide it with a codon frequency table.

Terminator

Searches for prokaryotic factor-independent RNA polymerase terminators according to the method of Brendel and Trifonov.

Motifs

Looks for sequence motifs by searching through proteins for the patterns defined in the PROSITE® Dictionary of Protein Sites and Patterns. Motifs can display an abstract of the current literature on each of the motifs it finds.

MEME (Multiple EM for Motif Elicitation) Finds conserved motifs in a group unaligned sequences. MEME saves these motifs as a set of profiles. A database search for sequences with similar profiles may be conducted using the Motif-Search program.

Repeat

Finds direct repeats in sequences. You must set the size, stringency, and range within which the repeat must occur; all the repeats of that size or greater are displayed as short alignments.

FindPatterns

Identifies sequences that contain short patterns like GAATTC or YRYRYRYR. The user may define the patterns ambiguously and allow mismatches or provide the patterns in a file or simply type them in from the terminal.

Composition

Determines the composition of sequence(s). For nucleotide sequence(s), Composition also determines dinucleotide and trinucleotide content.

CodonFrequency

Tabulates codon usage from sequences and/or existing codon usage tables. The output file is correctly formatted for input to the CodonPreference, Correspond, and Frames programs.

Correspond

Looks for similar patterns of codon usage by comparing codon frequency tables.

Window

Makes a table of the frequencies of different sequence patterns within a window as it is moved along a sequence. A pattern is any short sequence like GC or R or ATG. The sata output may be ploted with the program StatPlot.

StatPlot

Plots a set of parallel curves from a table of numbers like the table written by the Window program. The statistics in each column of the table are associated with a position in the analyzed sequence.

FitConsensus

Uses a consensus table written by Consensus as a probe to find the best examples of the consensus in a DNA sequence. The number of fits may be specified by the user and FitConsensus tabulates them with their position, frame, and a statistical measure of their quality.

Consensus,

Calculates a consensus sequence for a set of pre-aligned short nucleic acid sequences by tabulating the percent of G, A, T, and C for each position in the set. FitConsensus uses the Consensus output table as a probe to search for the best examples of the derived consensus in other nucleotide sequences.

Xnu

Replaces statistically significant tandem repeats in protein sequences with X characters. If a resulting protein sequence is used as a query for a BLAST search, the regions with X characters are ignored.

Seg

Replaces low complexity regions in protein sequences with X characters. If a resulting protein sequence is used as a query for a BLAST search, the regions with X characters are ignored.

Table VII Protein Analysis-Analysis Tools

Motifs

Looks for sequence motifs by searching through proteins for the patterns defined in the PROSITE® Dictionary of Protein Sites and Patterns. Motifs can display an abstract of the current literature on each of the motifs it finds.

ProfileScan

Uses a database of profiles to find structural and sequence motifs in protein sequences.

CoilScan

Locates coiled-coil segments in protein sequences.

HTHScan

Scans protein sequences for the presence of helix-turn-helix motifs, indicative of sequence-specific DNA-binding structures often associated with gene regulation.

SPScan

Scans protein sequences for the presence of secretary signal peptides (SPs).

PeptideSort

Shows the peptide fragments from a digest of an amino acid sequence. It sorts the peptides by weight, position, and HPLC retention at pH 2.1. and shows the composition of each peptide. It also prints a summary of the composition of the whole protein.

Isoelectric

Plots the charge as a function of pH for any peptide sequence.

PeptideMap

Creates a peptide map of an amino acid sequence.

PepPlot

Plots measures of protein secondary structure and hydrophobicity in parallel panels of the same plot.

PeptideStructure

Makes secondary structure predictions for a peptide sequence. The predictions include (in addition to alpha, beta, coil, and turn) measures for antigenicity, flexibility, hydrophobicity, and surface probability. PlotStructure displays the predictions graphically.

Plotstructure

Plots the measures of protein secondary structure in the output file from PeptideStructure. The measures may be shown on parallel panels of a graph or with a two-dimensional "squiggly" representation.

Moment

Makes a contour plot of the helical hydrophobic moment of a peptide sequence.

HelicalWheel

Plots a peptide sequence as a helical wheel to help you recognize amphiphilic regions.

Xnu

Replaces statistically significant tandem repeats in protein sequences with X characters. If a resulting protein sequence is used as a query for a BLAST search, the regions with X characters are ignored.

Seg

Replaces low complexity regions in protein sequences with X characters. If a resulting protein sequence is used as a query for a BLAST search, the regions with X characters are ignored.

The design tools 140 allow the user to select a gene sequence and design degenerate primers.

The design tools 140 may include a gene sequence A selection process 142 and a degenerate primer design process 144. The following analysis tools software is available from the Genetics Computer Group (GCG) software and may be accessed by the system of the present invention.

Table VIII Primer Selection-Design Tools

Prime

Selects oligonucleotide primers for a template DNA sequence. The primers may be useful for the polymerase chain reaction (PCR) or for DNA sequencing. Prime allows the user to choose primers from the whole template or limit the choices to a particular set of primers listed in a file.

Table IX Evolution-Design Tools

PAUPSearch

Provides a GCG interface to the tree-searching options in PAUP (Phylogenetic Analysis Using Parsimony). Starting with a set of aligned sequences, a search may be conducted for phylogenetic trees that are optimal ccording to parsimony, distance, or maximum likelihood criteria; reconstruct a neighbor-joining tree; or perform a bootstrap analysis.

Distances

Creates a table of the pairwise distances within a group of aligned sequences.

GrowTree

Creates a phylogenetic tree from a distance matrix created by Distances using either the UPGMA or neighbor-joining method. A text or graphics output file may be conducted.

Diverge

Estimates the pairwise number of synonymous and non-synonymous substitutions per site between two or more aligned nucleic acid sequences that code for proteins.

The cloning tools 150 allow the user to clone genetic material from the degenerate primers via cloning process 152 as described hereinbelow in the examples.

Figure 2:
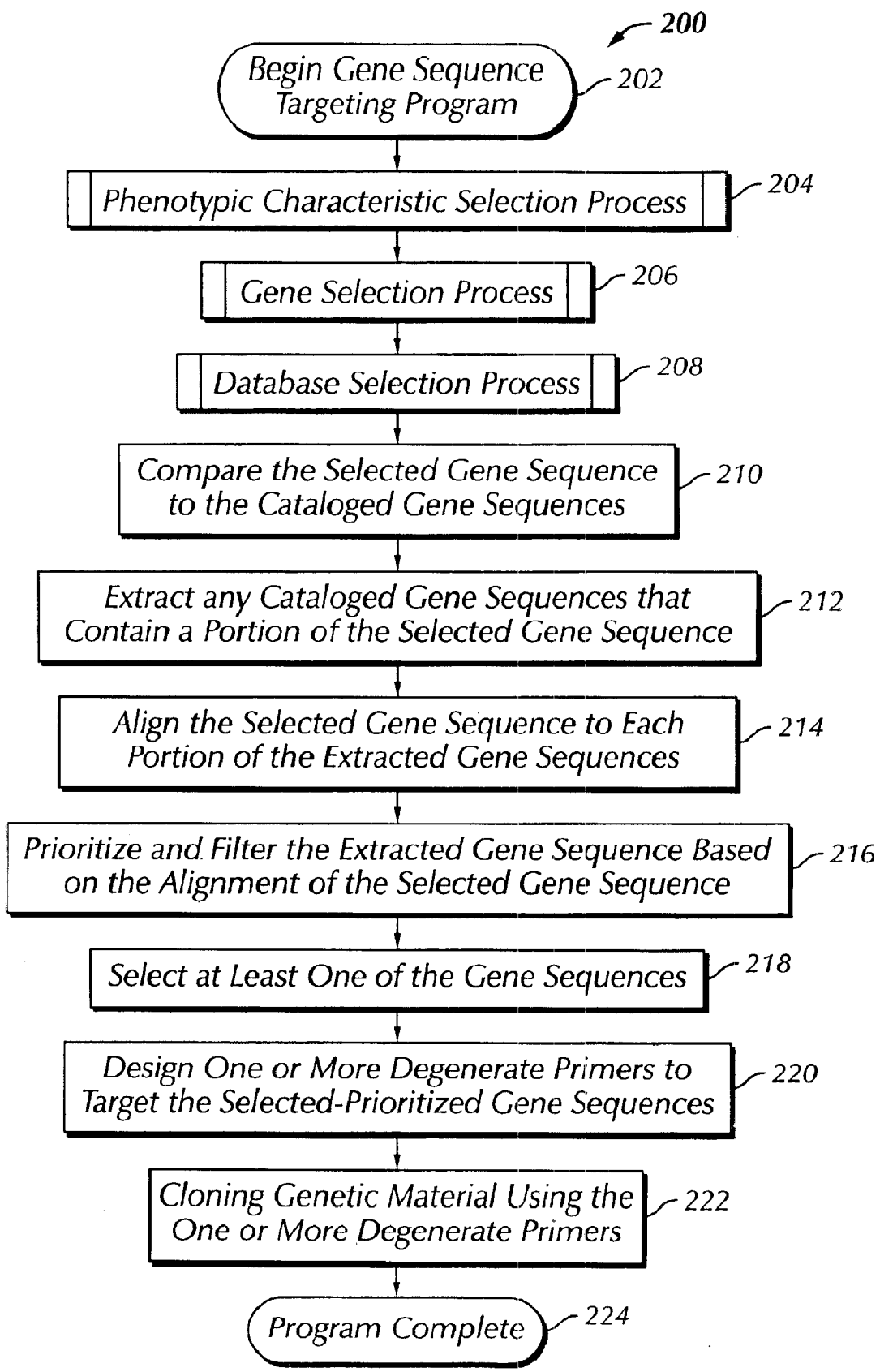
FIG. 2 is a basic flow chart showing a gene sequence targeting program in accordance with the present invention.

Now referring to FIG. 2, a basic flow chart shows a gene sequence targeting program 200 in accordance with the present invention. The gene sequence targeting program 200 begins in block 202. One or more phenotypic characteristics are selected using the phenotypic characteristic selection process (see FIG. 3) in block 204. A gene sequence that is known to have the selected phenotypic characteristics is selected using the gene sequence selection process (see FIG. 4) in block 206. One or more databases containing cataloged gene sequences are selected using the database selection process (see FIG. 5) in block 208.

The selected gene sequence is compared to the cataloged gene sequences in block 210, and any cataloged gene sequences that contain a portion of the selected gene sequence are extracted in block 212. The selected gene sequence is aligned to each portion of the extracted gene sequence in block 214 and the extracted gene sequences are prioritized and filtered based on the alignment of the selected gene sequence in block 216. At least one of the prioritized gene sequences is selected based on one or more phenotypic criteria in block 218. One or more degenerate primers are designed to target the selected-prioritized gene sequences in block 220, and genetic material is cloned using the one or more degenerate primers in block 222. The program is complete in block 224.

Figure 3:
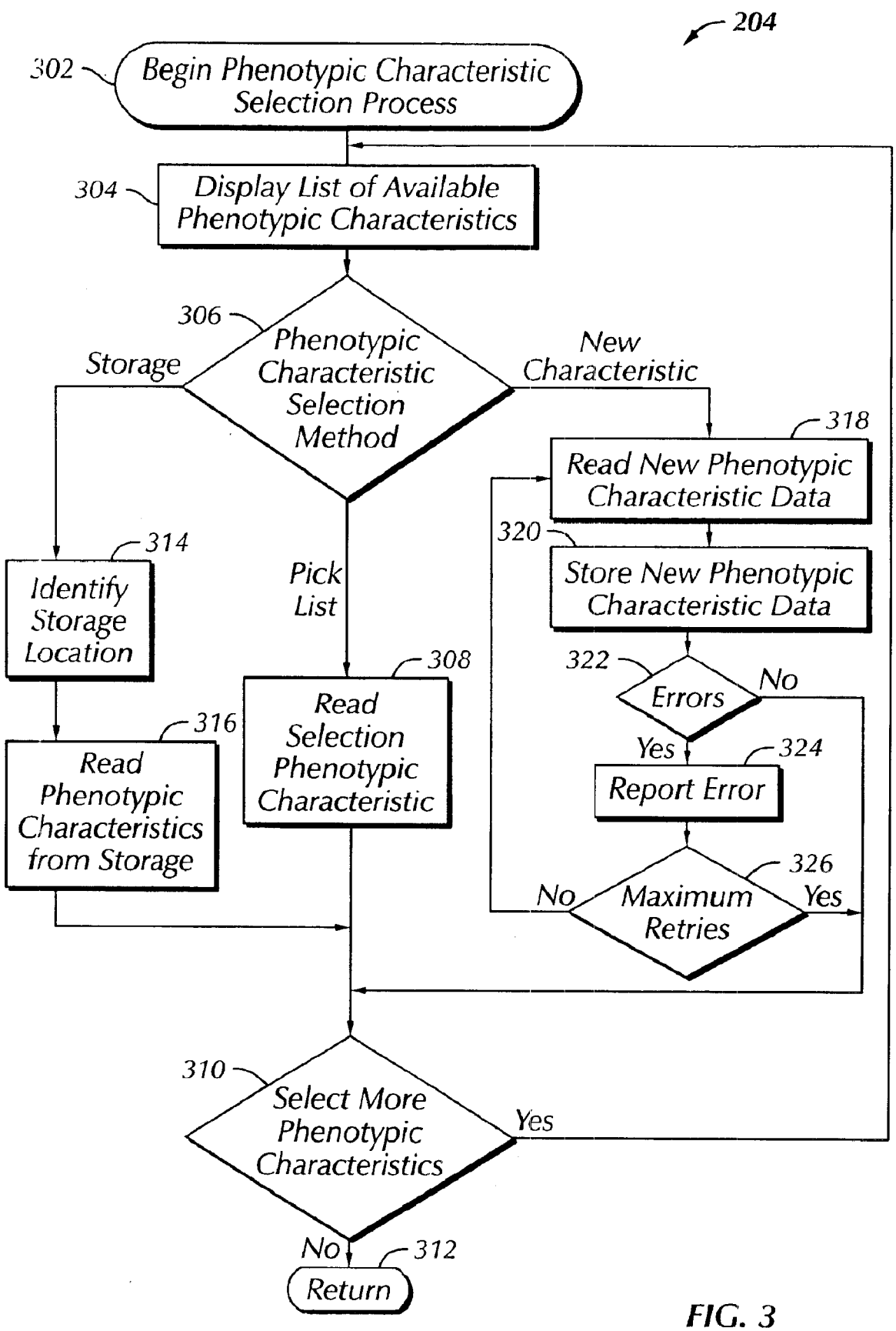
FIG. 3 is a flow chart showing the phenotypic characteristic selection process in accordance with the present invention.

Referring now to FIG. 3, a flow chart shows the phenotypic characteristic selection process 204 in accordance with the present invention. The phenotypic characteristic selection process 204 begins in block 302 and a list of available phenotypic characteristics is displayed to the user via the GUI 112 (FIG. 1) in block 304. The user can select one of the displayed phenotypic characteristics, read one or more phenotypic characteristics from storage, such as a data file, or create a new phenotypic characteristic selection option. If the user selects the option of picking one of the displayed phenotypic characteristics, as determined in decision block 306, the selected phenotypic characteristic is read in block 308. The user is then prompted to select additional phenotypic characteristics in block 310.

If the user selects the option of reading one or more phenotypic characteristics from storage, as determined in decision block 306, the user identifies the location of the stored data in block 314. The location of the stored data may be accessed locally via a disk drive or remotely via a network. The phenotypic characteristics are then read from storage in block 316. Standard error handling routines can be used to report status of the read operation, test the data, prompt the user for additional information, or indicate that the read was not successfully completed. The user is then prompted to select additional phenotypic characteristics in block 310.

If the user selects the option of creating a new phenotypic characteristic selection option, as determined in decision block 306, the new phenotypic characteristic data is read in block 318. This new data can be entered directly by the user or read from a file. The new phenotypic characteristic data is stored in block 320 and can be included in the list of available phenotypic characteristics displayed in block 304. If the new phenotypic characteristic data has errors or was not properly read and stored, as determined in decision block 322, the error is reported in block 324. If a maximum number of retry attempts has not occurred, as determined in decision block 326, the new characteristic process repeats by again reading the new phenotypic characteristic data in block 318. If, however, there are no errors, as determined in decision block 322, or the maximum number of retry attempts has occurred, as determined in decision block 326, the user is prompted to select additional phenotypic characteristics in block 310.

After the selected method is complete (see blocks 308, 316, 322 and 326)., the user may then elect to select additional phenotypic characteristics. If the user elects to select additional phenotypic characteristics, as determined in is decision block 310, the list of available phenotypic characteristics is displayed again in block 304 and the process repeats as previously described. If, however, the user elects to not select additional phenotypic characteristics, as determined in decision block 310, processing returns to the main program in block 312.

Figure 4:
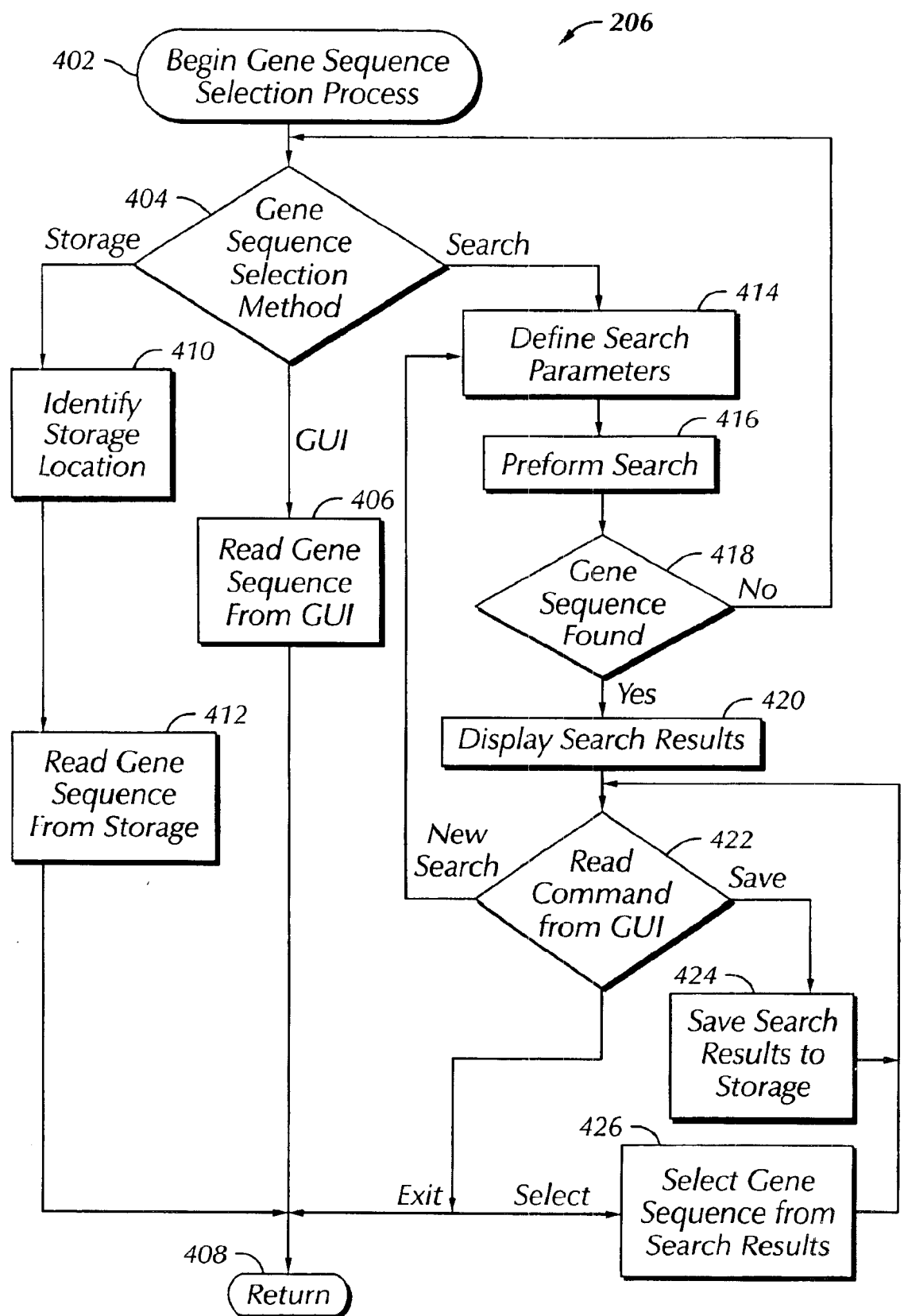
FIG. 4 is a flow chart showing the gene sequence selection process in accordance with the present invention.

Now referring to FIG. 4, a flow chart shows the gene sequence selection process 206 in accordance with the present invention. The gene selection process 206 begins in block 402. The user can enter a gene sequence using the GUI, read a gene sequence from storage, such as a data file, or search for all or part of a gene sequence. If the user selects the option of entering a gene sequence using the GUI, as determined in decision block 404, the gene sequence is read in block 406 and processing returns to the main program in block 408.

If the user selects the option of reading a gene sequence from storage, as determined in decision block 404, the user identifies the location of the stored data in block 410. The location of the stored data may be accessed locally via a disk drive or remotely via a network. The gene sequence is then read from storage in block 412 and processing returns to the main program in block 408. Standard error handling routines can be used to report status of the read operation, test the data, prompt the user for additional information, or indicate that the read was not successfully completed.

If the user selects the option of searching for all or part of a gene sequence, as determined in decision block 404, the search parameters, such as the database to be searched, are defined in block 414. The search is performed in block 416. If a gene sequence was not found, as determined in decision block 418, the user is again prompted to select a gene sequence selection method in block 404. If, however, a gene sequence was found, as determined in decision block 418, the search results are displayed in block 420. The user can then run a new search, save the search results, select a gene sequence from the search results or exit the selection process. If the user elects to run a new search, as determined in decision block 422, processing returns to block 414 where the search parameters are again defined. If the user elects to save the search results, as determined in decision block 422, the search results are then save to storage in block 424 and the user can then run a new search, save the search results, select a gene sequence from the search results or exit the selection process. If the user elects to select a gene sequence from the search results, as determined in decision block 422, the gene sequence is selected in block 426 and the user can then run a new search, save the search results, select a gene sequence from the search results or exit the selection process. If the user elects to exit the process, as determined in decision block 422, processing returns to the main program in block 408.

Figure 5:
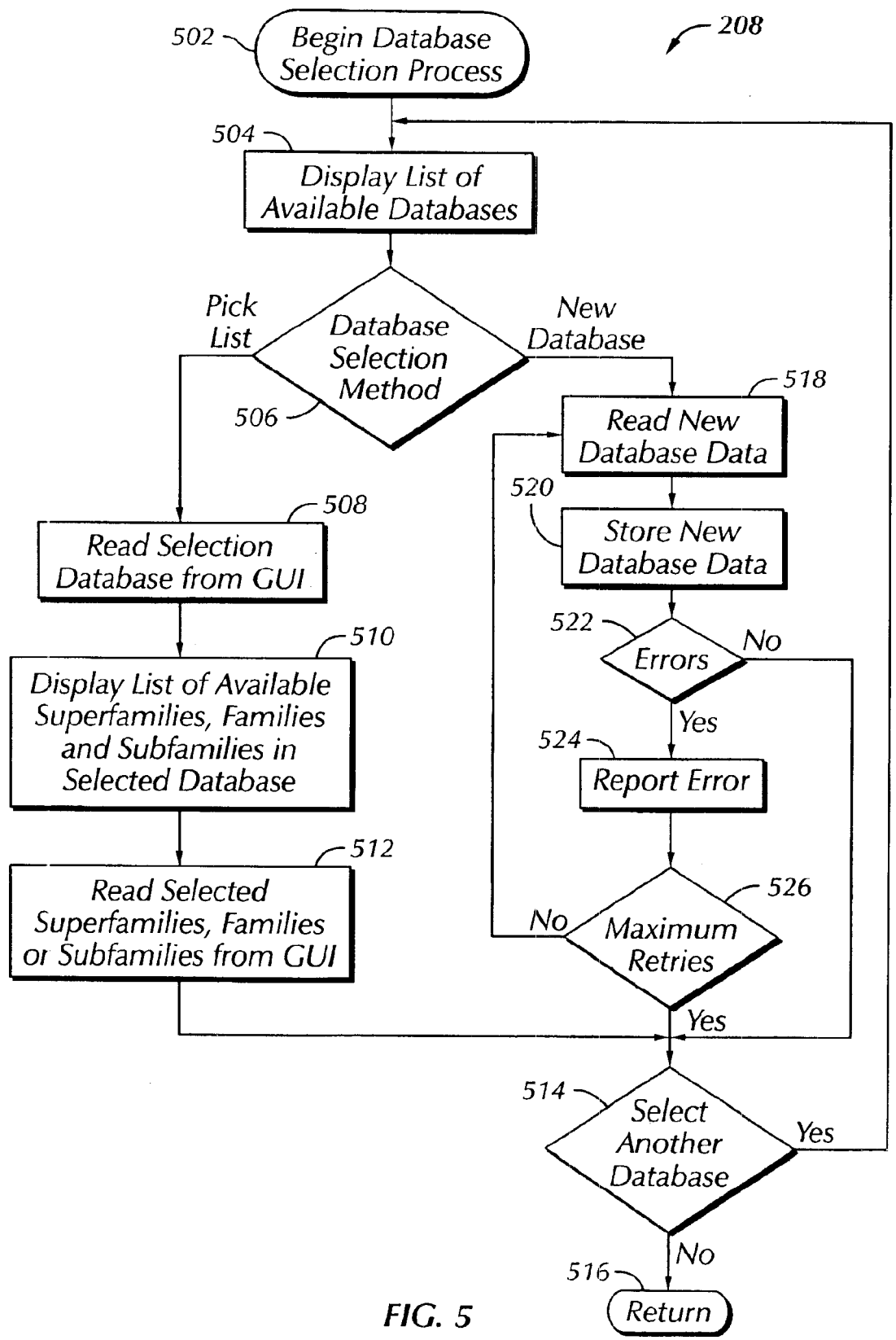
FIG. 5 is a flow chart showing the database selection process in accordance with the present invention.

Referring now to FIG. 5, a flow chart shows the database selection process 208 in accordance with the present invention. The database selection process 208 begins in block 502 and a list of available databases is displayed to the user via the GUI 112 (FIG. 1) in block 504. The user can select one of the displayed databases, or provide the necessary information to search a new database. If the user selects the option of picking one of the displayed databases, as determined in decision block 305, the database selection is read in block 508. A list of available superfamilies, families and subfamilies for the selected database is displayed in block 510 and the family selection is read in block 512. The user is then prompted to select additional databases in block 514.

If the user selects the option of providing the necessary information to search a new database, as determined in decision block 506, the data necessary to read the new database is read in block 518. This new data can be entered directly by the user or read from a file. The new database information is stored in block 520 and can be included in the is list of available databases displayed in block 504. If the new database information has errors or was not properly Us read and stored, as determined in decision block 522, the error is reported in block 524. If a maximum number of retry attempts has not occurred, as determined in decision block 526, the new database process repeats by again reading the information necessary to search the new database in block 518, if, however, there are no errors, as determined in decision block 522, or the maximum number of retry attempts has occurred, as determined in decision block 526, the user is prompted to select additional databases in block 514.

After the selected method is complete (see blocks 512, 522 and 526), the user may then elect to select additional databases. If the user elects to select additional databases, as determined in decision block 514, the list of available databases is displayed again in block 504 and the process repeats as previously described. If, however, the user elects to not select additional databases, as determined in decision block 514, processing returns to the main program in block 516.

It should be understood that all of the above processes are capable of being executed either on a single computer, or via a coordinating network of computers, each of which is capable of executing any of the described processes. It should further be understood that the invention set forth herein may be stored within computer memory, or on a hard drive or multiple hard drives of one or more computers, server or other media, e.g., CD-ROM or diskette.

A system of data mining tools has been developed to help identify, isolate and clone biologically and functionally important genes from public genomic libraries. The software suite called SPADE™, is designed to seamlessly integrate available search and analysis tools so that computer experiments for sequence analysis can be quickly designed and executed and that rational primer design, cloning and protein characterization can be accomplished.

Figure 6:
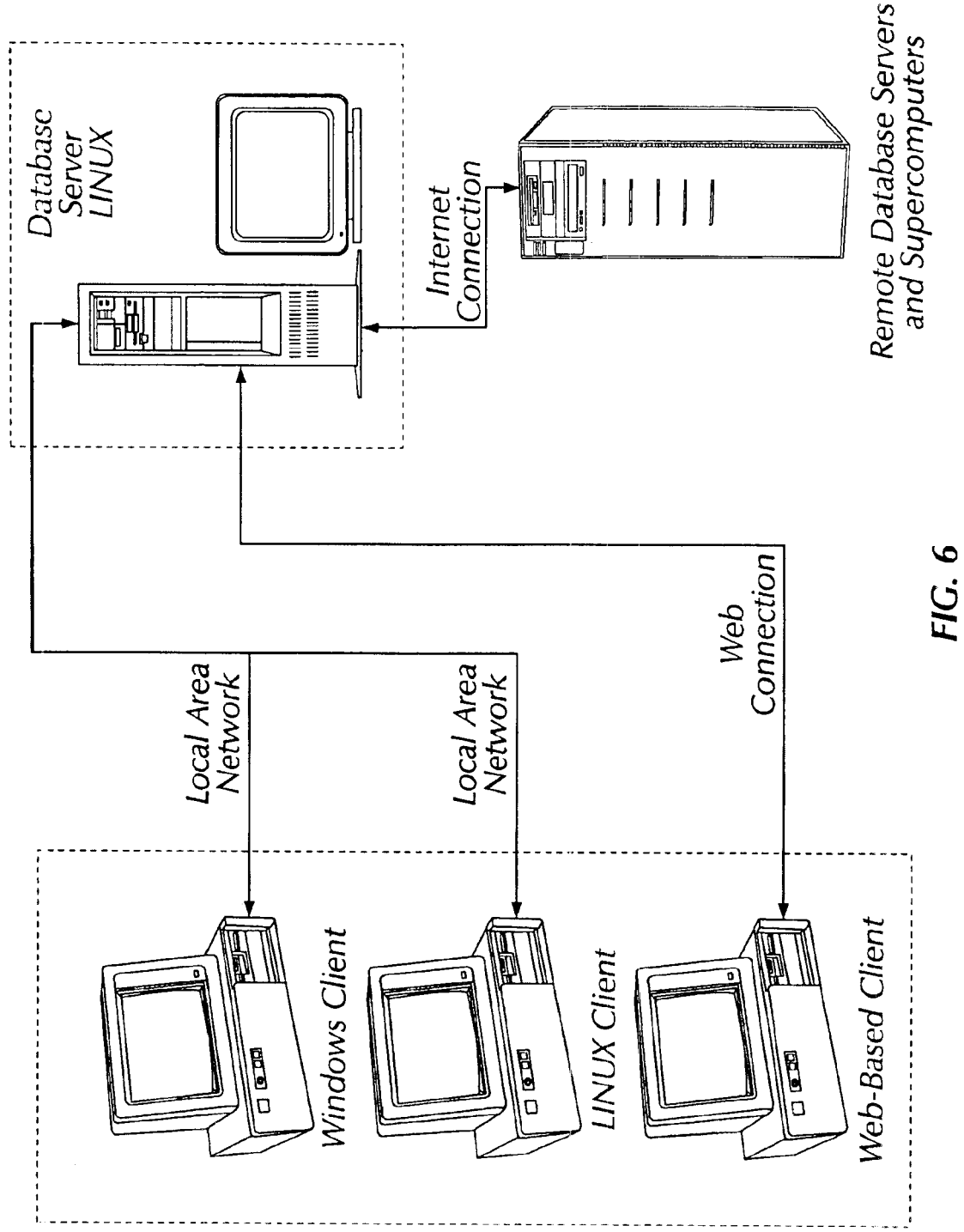
FIG. 6 provides the system network overview in the SPADE™ system.

SPADE™ is a client/server application. The clients interact with the server, which can be a dedicated LINUX server, via a local area network or a web interface. Therefore, the interaction is platform-free. An example of the system network overview is illustrated in FIG. 6.

Figure 7:
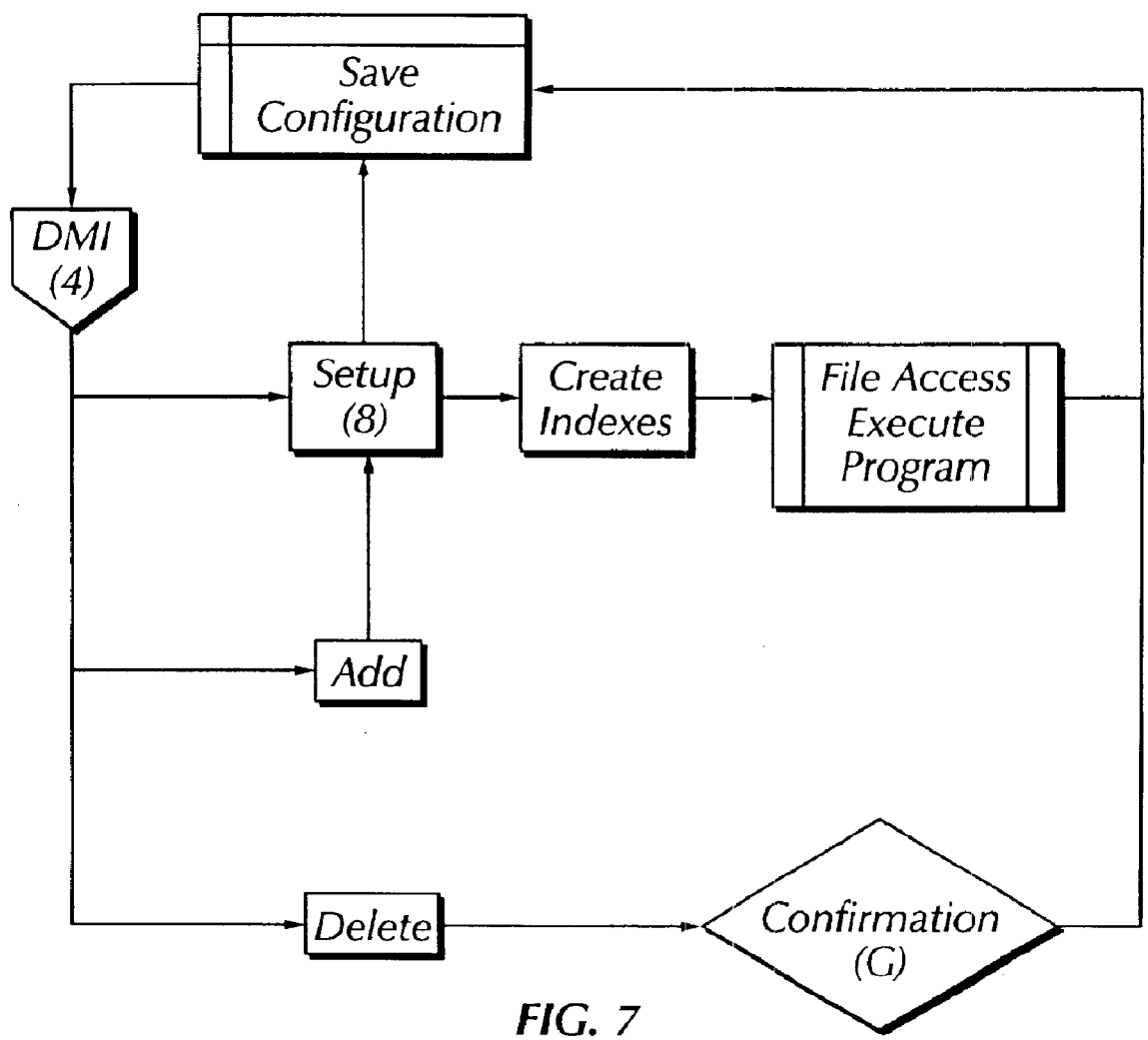
FIG. 7 provides the database management screen in the SPADE™ system.
Figure 8:
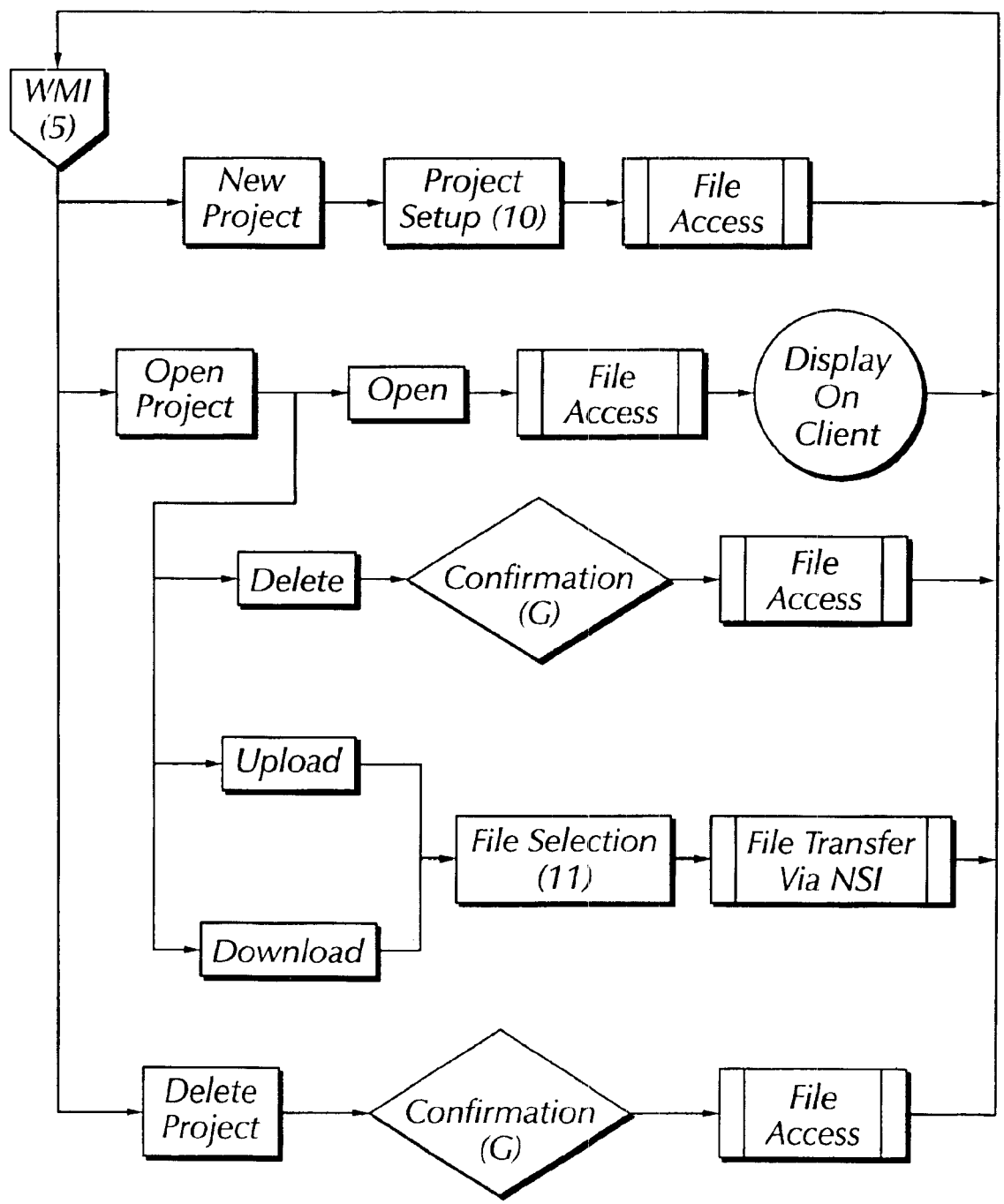
FIG. 8 provides the workspace management screen in the SPADE™ system.
Figure 9:
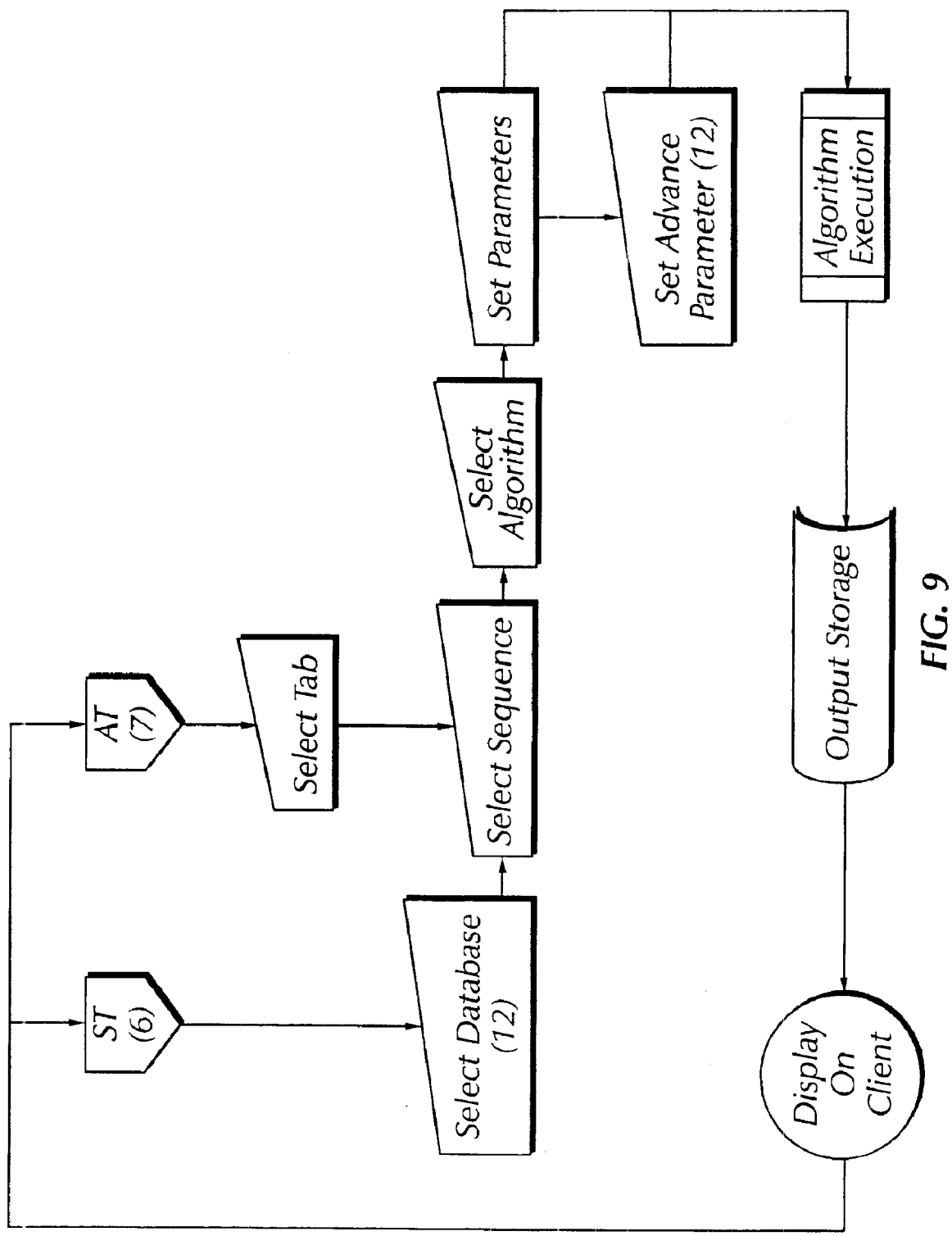
FIG. 9 provides the search analysis tools screen in the SPADE™ system.

The program flow is as follows: A user first logs in and is then presented with a main menu. The main menu presents four choices: Database Management (FIG. 7), Workspace Management (FIG. 8), Search Tools and Analysis Tools (FIG. 9). The Database Management screen allows the administrator of the system to con FIGURE the local genomic databases associated with SPADE™. In this screen, there is a list of current databases online, a button to edit the configuration for each individual database, and options to add new databases or delete existing databases. The Workspace Management screen allows the user to access his or her data, files and documentation on the server. It is similar to a file management program. There is a list of projects, and the files in the current project. The user can open a project, create new projects or delete existing projects. Within each project, the user can open individual data files, rename, delete, upload or download files. The search tool screen allows the user to search databases with the algorithms associated with SPADE™. The user first selects the database via a database selection window, and then selects the sequence to search from the project files or enters the sequence directly into the text box. The user then selects the algorithm to search, and accepts the default parameters or modifies the appropriate parameters. Users can access the advance parameters via the advance parameters screen. Finally, the server executes the search and returns the result to the user. The search tool screen also allows the user to analyze the results of the previous search or analysis with the algorithms associated with SPADE™. The user first selects the sequence to analyze from the project files or enters the sequence directly into the text box. The user then selects the algorithm to execute, and accepts the default parameters or modifies the appropriate parameters. Users can access the advance parameters via the advance parameters screen. Finally, the server executes the algorithm and returns the result to the user.

Figure 10:
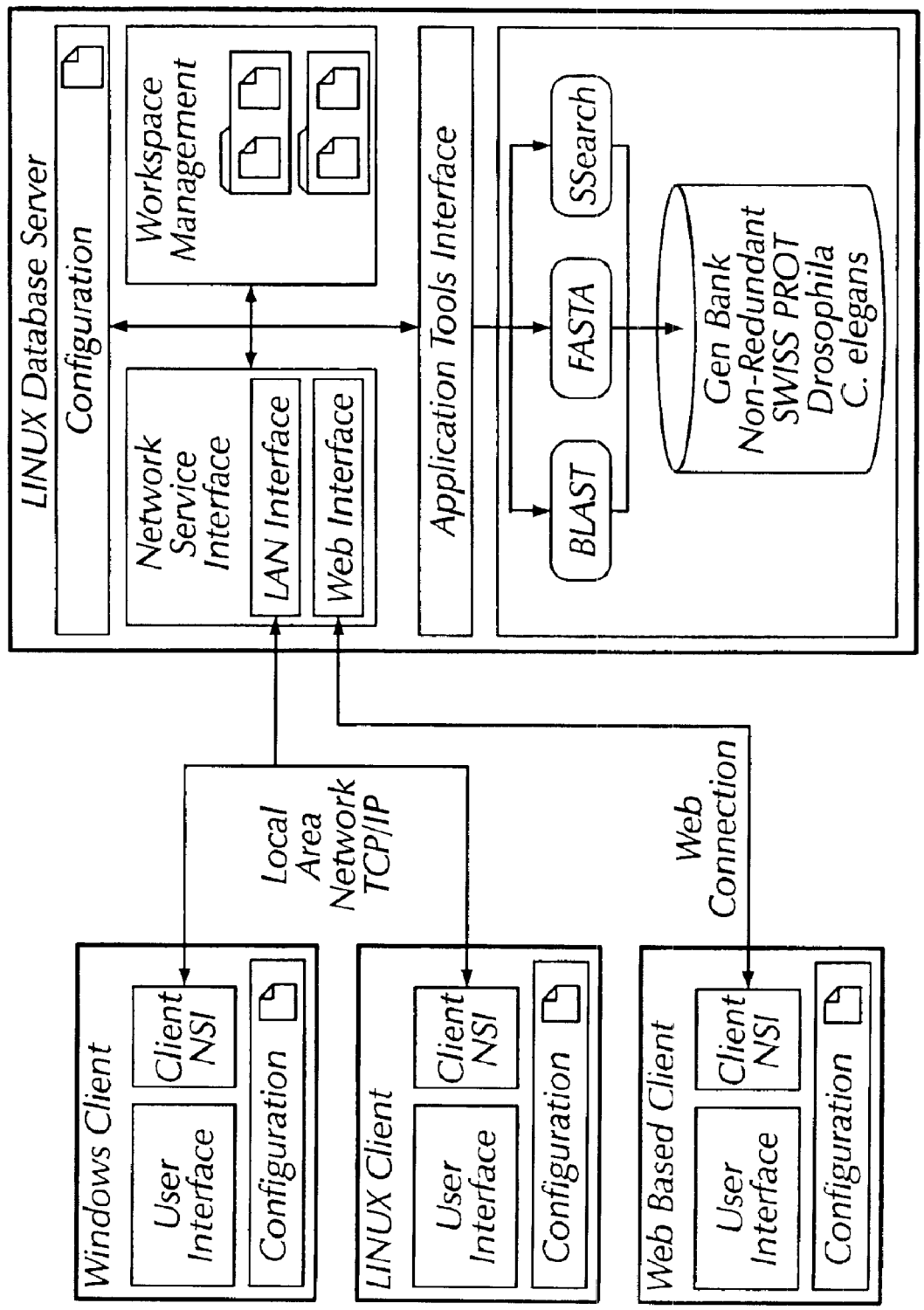
FIG. 10 provides the system architecture overview of the SPADE™ system.
Figure 11:
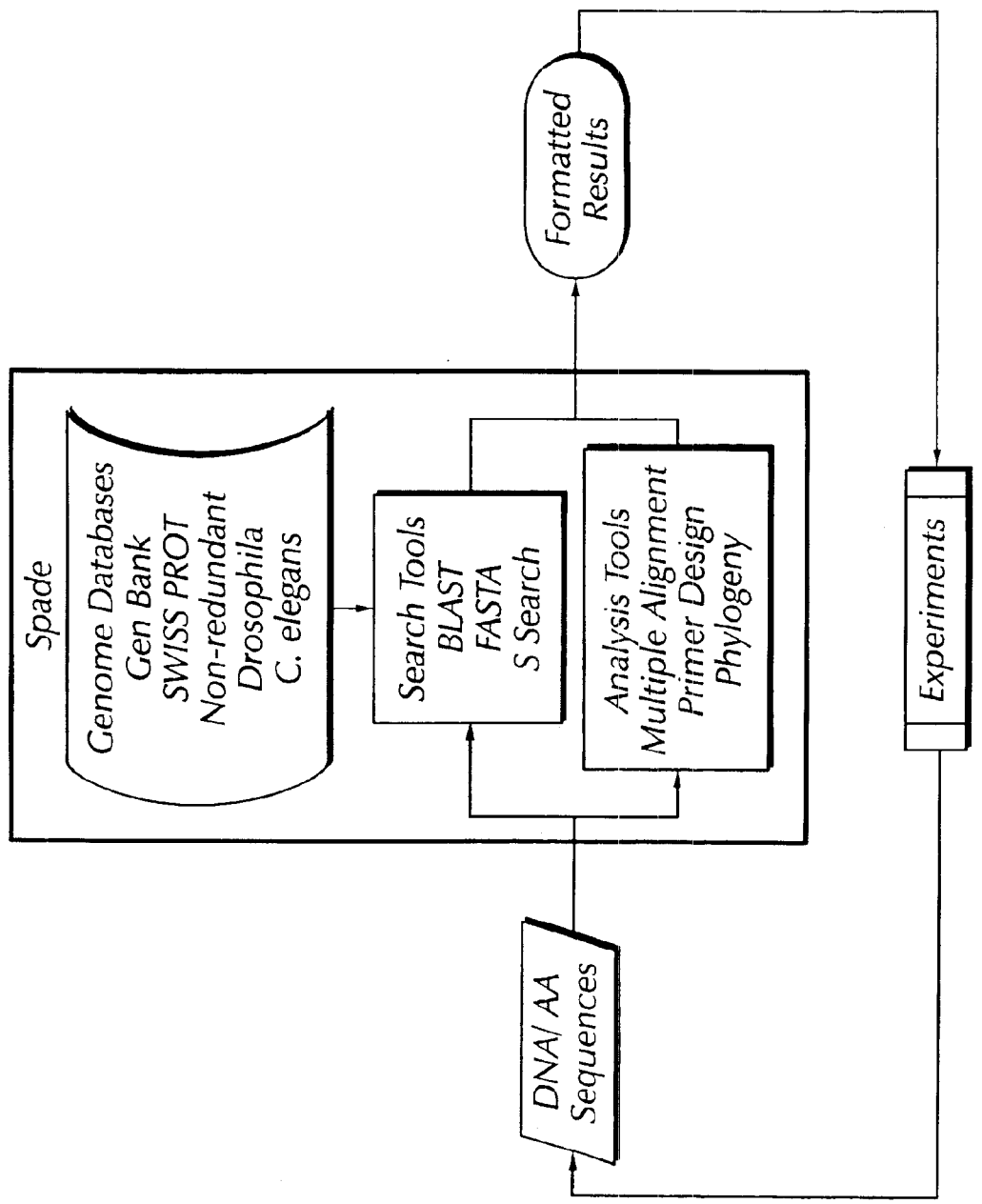
FIG. 11 provides an example of an application of the SPADE™ system.
Figure 12:
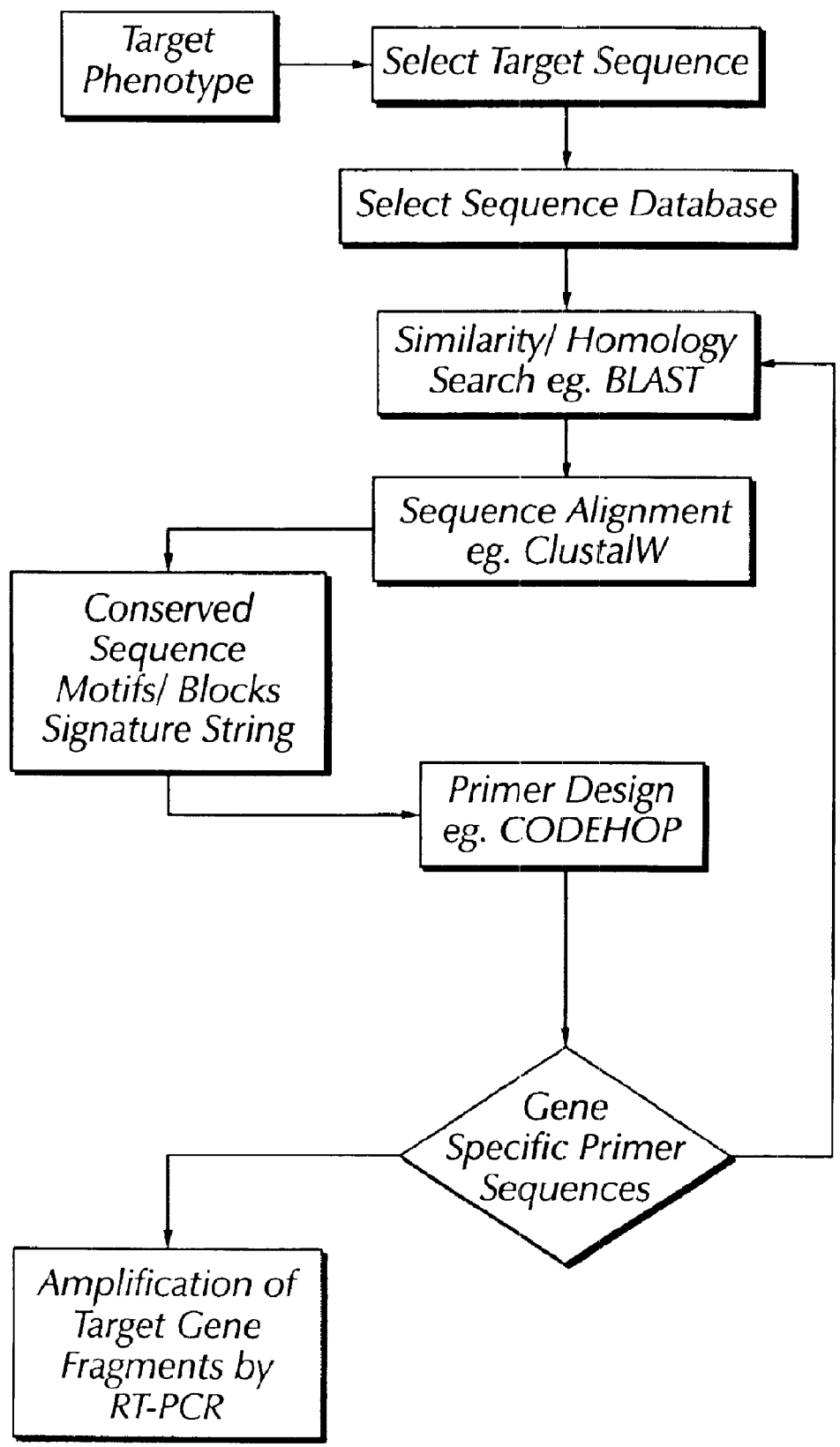
FIG. 12 provides an example of an application of the SPADE™ system.

An example of the system architecture overview is illustrated in FIG. 10, showing the interaction of the platform-free users with the four screens discussed above. FIG. 11 describes a use of the system described in FIG. 10. A mere specific example of the application is outlined in FIG. 12, which shows one possible use of the SPADE™ system.

The seamless integration of the various components described in the process flow discussed above, allows for the modification of existing components and the introduction of additional components which facilitate the characterization, targeting, cloning, validation, search and analysis, sorting, indexing, cataloging and conversion of various forms and formats of data and databases including, but not limited to, DNA sequences, amino acid sequences, DNA and protein motifs, images, patterns, and tertiary and quarternary structure including, atomic and molecular-level interactions. Therefore, the system described above may be used to perform high throughput database conversion, high specificity and high throughput selection of primers, as well as high specificity and high throughput positioning of protein and DNA structure and motifs. In addition, each of the various components described in the process flow discussed above may be used individually or in combination with the remaining components, thereby allowing for the delivery of results from an individual component or a combination of components, as desired.

EXAMPLE 1

Isolation of Nucleic Acid Molecules Related to Integrin

The integrin family of cell adhesion receptors plays a fundamental role in the processes involved in cell division, differentiation and movement. The extracellular domains of integrin alpha/beta heterodimers mediate cell-matrix and cell-cell contacts while their cytoplasmic tails associate with the cytoskeleton and integrins can transduce information bidirectionally. Studies have led to the identification of the ligand-binding region on the beta subunit and sequences in the cytoplasmic tails of the beta subunits that interact with cytoskeletal and signalling components. Green L. J. et al., The integrin beta subunit. Int J Biochem Cell Biol (1998) 30(2):179–84. Integrin beta 1 (ITGB1) is a subunit of type I membrane proteins and has cysteine rich domains that are involved in intrachain disulfide bonds. It associates with the alpha-1 or alpha-6 subunits to form a laminin receptor, with alpha-2 to form a collagen receptor, with alpha-4 to interact with vcam-1, with alpha-5 to form a fibronectin receptor and with alpha-8.

In order to demonstrate the system and method for identifying functional proteins in other target organisms, an integrin-like molecule most closely related to integrin beta 1 was identified and cloned from *Manduca sexta* (*M. sexta*). In this example, the original phenotypic characteristics selected were that the target molecule include a specific function and tissue localization. The specific function identified was that the target be an integral membrane protein involved in cytoskeletal formation. The localization selected was that the protein be expressed in the midgut of an organism.

These structural-functional parameters were then used to target potential genes based on the function identified from the PubMed database on all organisms (see FIG. 2). That is, the original search for a protein was not restricted by filtering.

Following the initial identification of a target and the filtering of sequences, an alignment of the beta integrin proteins that were identified from all organisms was conducted, and primer selection was made based on the identified matching sequences between the different organisms. The primer design software was the MacVector software, and following an initial round of sequence determination, the primer design was improved.

RT-PCR was conducted from *M. sexta* mRNA and following the PCR reaction a band of the expected size was cut out of a low-melt agarose gel. The PCR products were then cloned into the pAT vector and inserts sequenced. A BLAST alignment of the sequences identified a clone with similarity to *Pacifastacus leniusculus* (signal crayfish), *Drosophila* (fruit fly), *Anopheles gambiae* (African malaria mosquito) integrin beta 1 sequences.

The insert from these clones was then used to clone the full-length cDNA from an *M. sexta* library.

EXAMPLE 2

Isolation of a Known Gene to Validate System

In order to validate the system, it was used to isolate a known gene; in this case the *M. sexta* aminopeptidase gene. Aminopeptidase is involved in the modulation of various cellular responses, especially in cell-cell adhesion and signal transduction. We are particularly interested in aminopeptidase because we have shown that it is directly involved in resistance by insects to insecticidal toxins of *Bacillus thuringiensis*. We believe that it is a major factor involved in innate immunity of invertebrate and vertebrate epithelial cells. The *M. sexta* aminopeptidase gene was mined based on nucleotide and amino acid sequence alignment with the existing aminopeptidase related sequences, excluding the tobacco hornworm sequences. The primers used for PCR were based on such alignment.

Using this method, the tobacco hornworm aminopeptidase gene has been partially cloned and sequenced (not shown).

The amino acid sequence fragments showed high homology (99–100%) to GenBank Acc. No. P91885 (Denolf, P. et al., *Cloning and characterization of Manduca sexta and Plutella xylostella midgut aminopeptidase N enzymes related to Bacillus thuringiensis toxin-binding proteins* Eur. J. Biochem. 248(3), 748–761 (1997)). Thus, the gene mining technique has been proven to isolate a known gene.

EXAMPLE 3

Future Experiments

The above insect genes will be further characterized according to well established methods. Protein and peptide antibodies are made according to established protocols. The antibodies are used to confirm tissue and cellular localization of the expressed protein. The extent of homology of the identified genes with other insect species and other genera is checked by zooblot at varying hybridization stringencies.

The recombinant proteins are expressed, in for example, insect SF9 cells, and purified using the above antibodies, by GST or HIS tag immunoaffinity or by other means known in the art. The genes are mutated to prepare truncation mutants in order to delineate the boundaries of the functional proteins.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method to design primers which identify and target a first nucleotide sequence wherein the expression of said first nucleotide sequence results in at least one phenotypic characteristic, the method comprising the steps of:
    providing a second nucleotide sequence that is known to result in the phenotypic characteristic wherein the first nucleotide sequence and second nucleotide sequence are derived from different species;
    comparing the second nucleotide sequence to nucleotide sequences cataloged in one or more databases that annotate nucleotide sequences with phenotypic characteristics;
    extracting any cataloged nucleotide sequences that contain a portion of the second nucleotide sequence and which are annotated with said phenotypic characteristic;
    aligning the second nucleotide sequence to each extracted nucleotide sequence;
    prioritizing according to statistical analysis the extracted nucleotide sequences based on at least percent similarity with sequences having the highest percent similarity being highest in priority to ensure alignment to the second nucleotide sequence as determined by said statistical analysis; and
    designing one or more primers based on matching portions of the aligned prioritized sequences, which primers identify and target said first nucleotide sequence.

2. The method of claim 1, further comprising a step prior to the step of extracting cataloged nucleotide sequences of filtering the second nucleotide sequence to eliminate portions which are regions commonly found in encoding nucleotide sequences.

3. The method of claim 1, further comprising a step of cloning said first nucleotide sequence using the one or more designed primers.

4. The method of claim 1, wherein the one or more databases are selected from databases comprising catalogued sequences for humans, rats, mice, zebra fish, frogs, Drosophila, nematode, C. elegans, mosquito and bacteria.

5. The method of claim 1, wherein the one or more designed primers are nested.

6. The method of claim 1, wherein the second nucleotide sequence is aligned to each extracted nucleotide sequence by comparing deduced amino acid sequences.

7. The method of claim 1, wherein the second nucleotide sequence is aligned to each extracted nucleotide sequence by comparing the nucleotide sequences.

8. A system for designing primers which primers target a first nucleotide sequence wherein the expression of said first nucleotide sequence results in at least one phenotypic characteristic comprising:
    one or more computers collectively having program means thereon for performing the method of claim 1; and
    one or more databases containing the cataloged gene sequences; and
    a communication link connecting the computer or computers to said one or more databases.

9. The system of claim 8, wherein the program means comprises instructions for filtering the second nucleotide sequence to eliminate portions which are regions commonly found in encoding nucleotide sequences.

10. The system of claim 9, wherein the one or more databases are selected from databases comprising catalogued sequences for humans, rats, mice, zebra fish, frogs, Drosophila, nematode, C. elegans, mosquito and bacteria.

11. The system of claim 9, wherein the phenotypic characteristic is expression in insect mid-gut epithelium.

12. The system of claim 9, wherein the one or more designed primers are nested.

13. The system of claim 9, wherein the selected gene sequence is aligned to each extracted nucleotide sequence by comparing deduced amino acid sequences.

14. The system of claim 9, wherein the second nucleotide sequence is aligned to each extracted gene sequence by comparing nucleotide sequences.

15. A computer system embodied on a computer-readable medium for designing primers to identify and target a first nucleotide sequence wherein the expression of said first nucleotide sequence results in at least one phenotypic characteristic, said computer system comprising:
    means for providing a second nucleotide sequence that results in the phenotypic characteristic wherein the first nucleotide sequence and second nucleotide sequence are derived from different species;
    means for providing at least one database containing nucleotide sequences cataloged therein wherein said catalog annotates said sequences to resulting phenotypic characteristics;
    means for extracting from said at least one database a plurality of cataloged nucleotide sequences containing a portion of the said second nucleotide sequence and which are annotated with said phenotypic characteristic;
    means for aligning said second nucleotide sequence with said cataloged gene sequences;
    means for prioritizing according to statistical analysis the extracted gene sequences based on at least percent similarity with sequences having the highest percent similarity being highest in priority to ensure alignment with the second nucleotide sequence; and
    means for designing one or more primers based on matching portions of the aligned prioritized sequences, which primers identify and target said first nucleotide sequence.

16. The computer system of claim 15, further comprising a code segment for filtering the second nucleotide sequence to eliminate portions which are regions commonly found in encoding nucleotide sequences.

17. The computer program of claim 15, wherein the one or more databases are selected from databases comprising catalogued gene sequences for humans, rats, mice, zebra fish, frogs, Drosophila, nematode, C. elegans, mosquito and bacteria.

18. The computer system of claim 15, wherein the phenotypic characteristic is expression in insect mid-gut epithelium.

19. The computer system of claim 15, wherein the one or more designed primers are nested.

20. The computer system of claim 15, wherein the means for aligning the second nucleotide aligns each extracted nucleotide sequence by comparing deduced amino acid sequences.

* * * * *